(12) United States Patent
Shi

(10) Patent No.: US 9,498,477 B2
(45) Date of Patent: Nov. 22, 2016

(54) COMPOSITIONS AND USES THEREOF TO AMELIORATE PAIN

(71) Applicant: Purdue Research Foundation, West Lafayette, IN (US)

(72) Inventor: Riyi Shi, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 14/579,400

(22) Filed: Dec. 22, 2014

(65) Prior Publication Data
US 2015/0112061 A1    Apr. 23, 2015

Related U.S. Application Data

(63) Continuation of application No. 14/002,162, filed as application No. PCT/US2012/027421 on Mar. 2, 2012.

(60) Provisional application No. 61/448,703, filed on Mar. 3, 2011.

(51) Int. Cl.
  *A61K 31/5025*  (2006.01)
  *A61K 31/50*    (2006.01)
  *A61K 31/502*   (2006.01)

(52) U.S. Cl.
  CPC .......... *A61K 31/5025* (2013.01); *A61K 31/50* (2013.01); *A61K 31/502* (2013.01)

(58) Field of Classification Search
  CPC . A61K 31/5025; A61K 31/50; A61K 31/502
  See application file for complete search history.

(56) References Cited

U.S. PATENT DOCUMENTS

| 2002/0077328 A1 | 6/2002 | Hassan et al. |
| 2007/0087048 A1 | 4/2007 | Abrams et al. |

FOREIGN PATENT DOCUMENTS

WO    2005107467 A2    11/2005

OTHER PUBLICATIONS

Semeraro et al., Pharmacological studies on cadralazine: a new antihypertensive vasodilator drug, Journal of Cardiovascular Pharmacology (1981), 3(3), 455-67 CODEN: JCPCDT; ISSN: 0160-2446.
Ghilarducci DP, Tjeerdema RS (1995) Fate and effects of acrolein. Rev Environ Con tarn Toxicol 144:95-146.
Morell P, Quarles RH (1999) In: Basic Neurochemistry: Molecular, Cellular, and Medical Aspects (Siegel GJ, Agranoff BW, Alberts RW, Molinoff PB, eds). Philadelphia: Lippincott Williams & Wilkins.
PCT Search Report and Written Opinion for PCT/US2012/027421, completed Sep. 19, 2012.
Adams JD, Jr., Klaidman LK (1993) Acrolein-induced oxygen radical formation. Free Radical Biology & Medicine 15:187-193.
Basso et al. , Graded histological and locomotor outcomes after spinal cord confusion using the NYU weight-drop device versus transaction, Exp Neurol. 139:244-256 (1996).
Bautista D. M., Jordt S. E., Nikai T., Tsuruda P. R., REad A. J., Poblete J., Yamoah E. N., Basbaum A. I.., and Julius D. (2006) TRPA1 mediated the inflammatory actions of environmental irritants and proalgesic agents. Cell. 124, 1269-1282.
Burcham P. C., Kerr P. G., and Fontaine F. (2000) The antihypertensive hydralazine is an efficient scavenger of acrolein. Redox Rep. 5, 47-49.
Burcham PC, Fontaine FR, Kaminskas LM, Petersen DR, Pyke SM (2004) Protein adduct-trapping by hydrazinophthalazine drugs: mechanisms of cytoprotection against acrolein-mediated toxicity. Mol Pharmacol 65:655-664.
Burcham PC, Kaminskas LM, Fontaine FR, Petersen DR, Pyke SM (2002) Aldehyde-sequestering drugs: tools for studying protein damage by lipid peroxidation products. Toxicology 181-182:229-236.
Burcham PC, Kerr PG, Fontaine F (2000) The antihypertensive hydralazine is an efficient scavenger of acrolein. Redox Rep 5:47-49.
Burcham PC, Pyke SM (2006) Hydralazine inhibits rapid acrolein-induced protein oligomerization: role of aldehyde scavenging and adduct trapping in cross-link blocking and cytoprotection. Mol Pharmacol 69:1056-1065.
Compston A, Coles A (2008) Multiple sclerosis. Lancet 372:1502-1517.
Esterbauer H, Schaur RJ, Zollner H (1991) Chemistry and biochemistry of 4-20 hydroxynonenal, malonaldehyde and related aldehydes. Free Radical Biology & Medicine 11:81-128.
Gilgun-Sherki Y, Melamed E, Offen D (2004) The role of oxidative stress in the pathogenesis of multiple sclerosis: the need for effective antioxidant therapy, J. Neurol 251:261-268.
Gold R, Linington C, Lassmann H (2006) Understanding pathogenesis and therapy of multiple sclerosis via animal models: 70 years of merits and culprits in experimental autoimmune encephalomyelitis research. Brain 129:1953-1971.
Halliwell B, Gutteridge JMC. (1999) Free radicals in biology and medicine. Oxford: Oxford University Press.
Hamann K, Durkes A, Ouyang H, Uchida K, Pond A, Shi R (2008b) Critical role 5 of acrolein in secondary injury following ex vivo spinal cord trauma. J Neurochem 107:712-721.
Hamann K, Nehrt G, Ouyang H, Duerstock B, Shi R (2008a) Hydralazine inhibits compression and acrolein-mediated injuries in ex vivo spinal cord. J Neurochem 104:708-718.
Hamann K, Shi R (2009) Acrolein scavenging: a potential novel mechanism of attenuating oxidative stress following spinal cord injury. J Neurochem 111:1348-1356.

(Continued)

*Primary Examiner* — Paul V Ward
(74) *Attorney, Agent, or Firm* — Brown Rudnick LLP; Adam M. Schoen

(57) ABSTRACT

Hydrazinopyridazines, fused hydrazinopyridazines, phenylethylhydrazines, or combinations thereof, compositions comprising hydrazinopyridazines, fused hydrazinopyridazines, phenylethylhydrazines, or combinations thereof, and methods for using them for the treatment of pain are described.

17 Claims, 5 Drawing Sheets

(56) References Cited

OTHER PUBLICATIONS

Hamann K., Nehrt G., Ouyang H., Duerstock B., and Shi R. (2008) Hydralazine inhibits compression and acrolein-mediated injuries in ex vivo spinal cord. (J. Neurochem. 104, 708-718.

Kalyvas A, David S (2004) Cytosolic phospholipase A2 plays a key role in the pathogenesis of multiple sclerosis-like disease. Neuron 41:323-335.

Kaminskas LM, Pyke SM, Burcham PC (2004a) Reactivity of hydrazinophthalazine drugs with the lipid peroxidation products acrolein and crotonaldehyde. Org Biomol Chem 2:2578-2584.

Kaminskas LM, Pyke SM, Burcham PC (2004b) Strong protein adduct trapping accompanies abolition of acrolein-mediated hepatotoxicity by hydralazine in mice. J Pharmacol Exp Ther 310:1003-1010.

Kehrer JP, Biswal SS (2000) The molecular effects of acrolein. Toxicological Sciences 57:6-15.

Leung G., Sun W., Zheng L., Brookes S., Tully M., and Shi R. (2011) Anti-acrolein treatment improves behavioral outcome and alleviates myelin damage in EAE mouse. 173:150-155.

Liu-Snyder P, Borgens R. B., and Shi R. (2006) Hydralazine rescues PC12 cells from acrolein-mediated death. J Neurosci Res 84:219-227.

Liu-Snyder P, McNally H, Shi R, Borgens RB (2006) Acrolein-mediated mechanisms of neuronal death. J Neurosci Res 84:209-218.

Lovell MA, Xie C, Markesbery WR (2001) Acrolein is increased in Alzheimer's 20 disease brain and is toxic to primary hippocampal cultures. Neurobiology of Aging 22:187-194.

Luo J, Robinson JP, Shi R (2005b) Acrolein-induced cell death in PC 12 cells: role of mitochondria-mediated oxidative stress. Neurochem Int 47:449-457.

Luo J, Shi R (2004) Acrolein induces axolemmal disruption, oxidative stress, and mitochondrial impairment in spinal cord tissue. Neurochemsitry International 44:475-486.

Luo J, Shi R (2005) Acrolein induces oxidative stress in brain mitochondria. Neurochem Int 46:243-252.

Luo J, Uchida K, Shi R (2005a) Accumulation of acrolein-protein adducts after traumatic spinal cord injury. Neurochem Res 30:291-295.

Luo J., Uchida K, and Shi R. (2005) Accumulation of acrolein-protein adducts after traumatic spinal cord injury. Neurochem Res. 30, 291-295.

Montine TJ, Neely MD, Quinn JF, Beal MF, Markesbery WR, Roberts LJ, 30 Morrow JD (2002) Lipid peroxidation in aging brain and Alzheimer's disease. Free Radic Biol Med 33:620-626.

Pathak et al., Enzymic protecting group techniques in organic syntesis, Stereosel. Biocatal. 775-797 (2000).

Shao B, Fu X, McDonald TO, Green PS, Uchida K, O'Brien KD, Oram JF, 5 Heinecke JW (2005b) Acrolein impairs ATP binding cassette transporter Al-dependent cholesterol export from cells through site-specific modification of apolipoprotein A-T. J Biol Chem 280:36386-36396.

Shao B, O'Brien K D, McDonald TO, Fu X, Oram JF, Uchlda K, Heinecke JW (2005a) Acrolein modifies apolipoprotein A-I in the human artery wall. Ann N Y Acad Sci 1043:396-403.

Shao C, Roberts KN, Markesbery WR, Scheff SW, Lovell MA (2006) Oxidative stress in head trauma in aging. Free Radic Biol Med 41:77-85.

Shi R, Luo J, Peasley MA (2002) Acrolein inflicts axonal membrane disruption and conduction loss in isolated guinea pig spinal cord. Neuroscience 115:337-340.

Shibata N, Nagai R, Miyata S, Jono T, Horiuchi S, Hirano A, Kato S, Sasaki S, Asayama K, Kobayashi M (2000) Nonoxidative protein glycation is implicated in familial amyotrophic lateral sclerosis with superoxide dismutase-1 mutation. Acta Neuropathol (Berl) 15 100:275-284.

Shields DC, Banik NT (1999) Pathophysiological role of calpain in experimental demyelination. J Neurosci Res 55:533-541.

Shields DC, Schaecher KE, Saido TC, Banik NL (1999) A putative mechanism of demyelination in multiple sclerosis by a proteolytic enzyme, calpain. Proc Natl Acad Sci U S 20 A 96:11486-11491.

Smith KJ, Kapoor R, Felts PA (1999) Demyelination: the role of reactive oxygen and nitrogen species. Brain Pathol 9:69-92.

Trapp BD, Nave KA (2008) Multiple sclerosis: an immune or neurodegenerative disorder? Annu Rev Neurosci 31:247-269.

Trapp BD, Peterson J, Ransohoff RM, Rudick R, Mork S, Bo L (1998) Axonal transection in the lesions of multiple sclerosis. N Engl J Med 338:278-285.

Trapp BD, Ransohoff R, Rudick R (1999) Axonal pathology in multiple sclerosis: relationship to neurologic disability. Curr Opin Neurol 12:295-302.

Uchida K, Kanematsu M, Morimitsu Y, Osawa T, Noguchi N, Niki E (1998a) Acrolein is a product of lipid peroxidation reaction. Formation of free acrolein and its conjugate with lysine residues in oxidized low density lipoproteins. J Biol Chem 273:16058-16066.

Uchida K, Kanematsu M. Sakai K, Matsuda T, Hattori N, Mizuno Y, Suzuki D, Miyata T, Noguchi N, Niki E, Osawa T (1998b) Protein-bound acrolein: potential markers for oxidative stress. Proceedings of the National Academy of Sciences of the United States of 35 America 95:4882-4887.

Wood PL, Khan MA, Moskal JR, Todd KG, Tanay YA, Baker G (2006) Aldehyde load in ischemia-reperfusion brain injury: neuroprotection by neutralization of reactive aldehydes with phenelzine. Brain Res 1122:184-190.

Owen et al., Pharmacological properties of the stereoisomers of prizidilol: their use in analysis of reflex tachycardia nad blood pressure control in normotensive cats, rat, and dogs. Journal of Cardiovascular Pharmacology (1986), 8(4), 743-8 CODEN: JCPCDT; ISSN:0160-2446; English.

Monge et al. 1-Hydrazinopyridazino[4,5]quinoxaline, a new antihypertensive agent, European Journal of Medicine Chemistry (1986), 21(3) 251-4 CODEN: EJMCA5; ISSN: 0223-5234; English.

Watanabe et al, An analysis of blood pressure effects of nipradilol and prizidilol in normotensive and spontaneously hypertensive rats, Japanese Journal of Pharmacology (1985) 38(3) 273-9 CODEN: JJPAAZ; ISSN: 0021-5198; English.

COMPOSITIONS AND USES THEREOF TO AMELIORATE PAIN

CROSS REFERENCE TO RELATED APPLICATIONS

This application is a continuation of U.S. Non-provisional application Ser. No. 14/002,162 filed on Aug. 29, 2013, which is a 35 U.S.C. §371 national phase application of PCT International Application No. PCT/US2012/027421 filed on Mar. 2, 2012, which claims the benefit under 35 U.S.C. §119(e) of U.S. Provisional Application Ser. No. 61/448,703 filed on Mar. 3, 2011 the entire disclosure of each of which is incorporated herein by reference.

TECHNICAL FIELD

The invention described herein pertains to the treatment of pain.

BACKGROUND AND SUMMARY OF THE INVENTION

It has been discovered that in vivo production of acrolein may cause and/or exacerbate pain, such as pain due to disease or injury. It has also been discovered herein that compounds capable of interacting with acrolein are efficacious in treating pain. Without being bound by theory, it is believed herein that compounds that are capable of scavenging and/or preventing acrolein from activating pain relay systems, such as those found on dorsal root ganglion, and other sensory neurons, are efficacious in treating pain. Further, and without being bound by theory, it is believed herein that the compounds described herein capable of blocking the interaction of acrolein with pain relay receptors, such as Transient Receptor Potential Ankyrin 1 (TRPA1), are efficacious in treating pain. In particular, the invention described herein pertains to the treatment of pain using compounds that decrease and/or block the action of ligands and antagonists.

Acrolein, a reactive α,β-unsaturated aldehyde, has been reported to be a product of oxidative stress and lipid peroxidation. Furthermore, acrolein has been reported to remain active in the body for several days (Ghilarducci and Tjeerdema, 1995) while more commonly studied oxidative species decay within seconds (Halliwell and Gutteridge, 1999). Described herein is the role of acrolein in the pain using a well-established animal model of injury.

It has also been discovered that hydrazinopyridazines, fused hydrazinopyridazines, phenylethylhydrazines, and combinations thereof are useful in treating pain caused by disease and/or injury. Illustrative disease based pain includes allodynia, pain associated with MS, pain associated with neuropathy, such as pain associated with diabetes, and the like. Illustrative injury based pain includes neuronal injury such as spinal cord injury (SCI), spinal cord contusion injury, and the like. Additional illustrative disease-based pain or injury-based pain includes inflammatory pain, cancer pain, postoperative pain, and idiopathic pain (i.e. pain of unknown origin), for example, phantom limb pain. In one aspect, neuropathic pain includes pain caused by injury or infection of peripheral sensory nerves. Illustrative examples of neuropathic pain include, but are not limited to pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Neuropathic pain includes, but is not limited to pain caused by nerve injury such as, for example, the pain diabetics suffer from. It has also been discovered that compounds described herein are useful in decreasing or blocking the action of acrolein at TRPA1. Without being bound by theory, it is believed herein that the ligand binding properties, and more importantly the agonist properties of acrolein are decreased or by the compounds described herein. It has been discovered herein that injury may upregulate acrolein production, illustratively neuronal injury such as spinal cord injury (SCI), and the pain caused thereby is mediated by acrolein production. It has been discovered that the compounds described herein are capable of decreasing or blocking the pain associated with acrolein, including increased acrolein production following injury.

In one illustrative embodiment of the invention, compounds of the following formula are described herein:

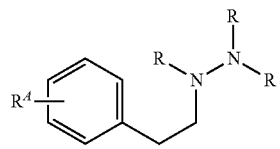

and pharmaceutically acceptable salts thereof, wherein:

R is independently selected in each instance from hydrogen, acyl, or sulfonyl; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; and $R^A$ represents three substituents selected from the group consisting of hydrogen, halo, hydroxy and derivatives thereof, amino and derivatives thereof, thio and derivatives thereof, acyl, carboxylate or a derivative thereof, hydroxylamino and derivatives thereof, hydrazino and derivatives thereof, sulfinyl or a derivative thereof, or sulfonyl or a derivative thereof; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; or two of $R^A$ are taken together with the attached carbons to form an optionally substituted saturated, unsaturated, or aromatic carbocycle or heterocycle.

In one illustrative embodiment of the invention, compounds of the following formula are described herein:

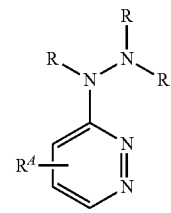

and pharmaceutically acceptable salts thereof, wherein:

R is independently selected in each instance from hydrogen, acyl, or sulfonyl; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; and $R^A$ represents three substituents selected from the group consisting of hydrogen, halo, hydroxy and derivatives thereof, amino and derivatives thereof, thio and derivatives thereof, acyl, carboxylate or a derivative thereof, hydroxylamino and derivatives thereof, hydrazino and derivatives thereof, sulfinyl or a derivative thereof, or sulfonyl or a derivative thereof; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; or two of $R^A$ are taken together with the attached carbons to form an optionally substituted saturated, unsaturated, or aromatic carbocycle or heterocycle.

In another embodiment, pharmaceutical compositions containing one or more of the compounds are also described herein. In one aspect, the compositions include a therapeutically effective amount of the one or more compounds for treating pain in a patient. It is to be understood that the compositions may include other component and/or ingredients, including, but not limited to, other therapeutically active compounds, and/or one or more carriers, diluents, excipients, and the like. In another embodiment, methods for using the compounds and pharmaceutical compositions for treating patients having pain are also described herein. In one aspect, the methods include the step of administering one or more of the compounds and/or compositions described herein to a patient having pain. In another aspect, the methods include administering a therapeutically effective amount of the one or more compounds and/or compositions described herein for treating patients having pain. In another embodiment, uses of the compounds and compositions in the manufacture of a medicament for treating patients having pain are also described herein. In one aspect, the medicaments include a therapeutically effective amount of the one or more compounds and/or compositions for treating a patient having pain. In another embodiment, unit doses and/or unit dosage forms that include the compounds and pharmaceutical compositions for treating patients having pain are also described herein. In another aspect, the unit doses and/or unit dosage forms are administered to a patient having pain.

It is appreciated herein that the compounds described herein may be used alone or in combination with other compounds useful for treating pain, including those compounds that may be therapeutically effective by the same or different modes of action. In addition, it is appreciated herein that the compounds described herein may be used in combination with other compounds that are administered to treat other symptoms that may accompany or be accompanied by pain.

Hydralazine, a fused hydrazinopyridazine, is an illustrative compound that may be included in the pharmaceutical compositions, unit dosage forms, methods, and uses described herein. Hydralazine is an effective acrolein scavenger and is used to trap acrolein, which is significantly increased following injury. Hydralazine treatment appears to alleviate pain, and tends to lower acrolein levels in injured tissue, such as spinal cord. Without being bound by theory, it is believed herein that the ability of hydralazine to treat pain is due at least in part to its capability of interacting with, blocking, or otherwise intervening in the pathology of acrolein. Additional illustrative hydrazinopyridazines and fused hydrazinopyridazines useful in the methods, uses, formulations, and unit dosage forms described herein include, but are not limited to:

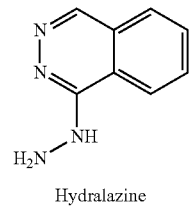
Hydralazine

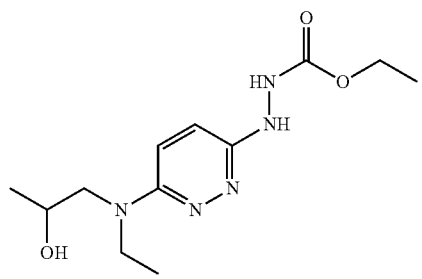
Cadralazine

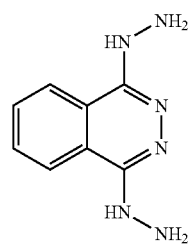
Dihydralazine

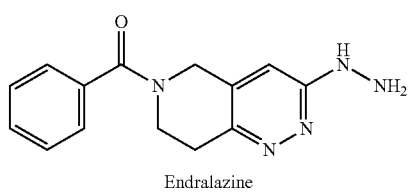
Endralazine

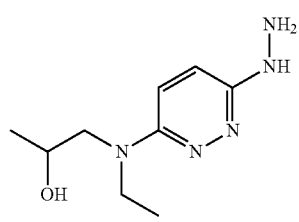
Pidralazine

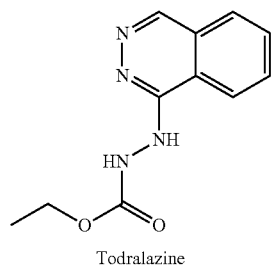
Todralazine

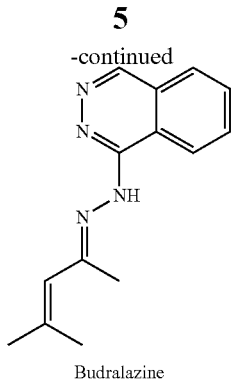
Budralazine and analogs and derivatives thereof.

DETAILED DESCRIPTION

Figure 1:
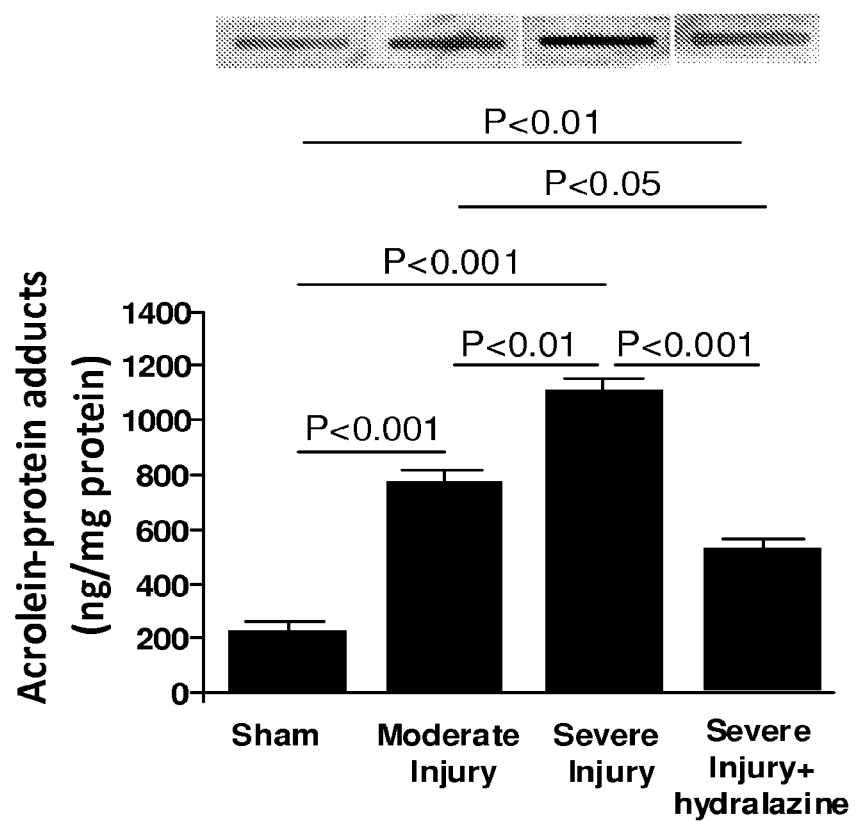
FIG. 1. Effect of treatment with hydralazine on acrolein-protein adducts. Hydralazine is applied systemically through a single intraperitoneal injection at a dose of 5 mg/kg body weight. The relative densities of samples in the upper part of the figure are converted to concentrations based on standard curves. Quantitative analysis (n=4 in all cases) indicates that both moderate and severe contusion injuries produced graded and significant elevation of acrolein. Hydralazine reduced acrolein levels in severe contusion injuries.

In one embodiment, described herein is a method for treating a patient with pain, the method comprising the step of administering to the patient a therapeutically effective amount of one or more hydrazinopyridazines, fused hydrazinopyridazines, phenylethylhydrazines, or combinations thereof.

In another embodiment, described herein is a method for treating a patient with pain, the method comprising the step of administering to the patient a therapeutically effective amount of one or more compounds of the formula

wherein a, b, and c are independently a single or a double bond; $R^1$ and $R^2$ are each independently hydrogen or alkyl, $C(O)OR^E$, or optionally substituted heteroaryl, where $R^E$ is alkyl, heteroalkyl, aryl, heteroaryl, alkylaryl, alkylheteroaryl, each of which is optionally substituted; and $R^3$ and $R^4$ are each independently a lone pair of electrons or a hydrogen, where at least one of $R^1$, $R^2$, $R^3$, or $R^4$ is not a hydrogen; and where each of the bonds connecting $R^1$ to N, N to N, and N to $R^2$ is independently a single, a double, or an aromatic bond, providing that the bond connecting N to N is not a double bond when either other bond is a double bond.

In another embodiment, described herein is a method as described above wherein the phenylethylhydrazine is a compound of the formula

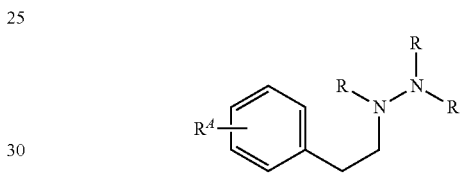

or a pharmaceutically acceptable salt thereof, wherein:

R is independently selected in each instance from hydrogen, acyl, or sulfonyl; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; and $R^A$ represents three substituents selected from the group consisting of hydrogen, halo, hydroxy and derivatives thereof, amino and derivatives thereof, thio and derivatives thereof, acyl, carboxylate or a derivative thereof, hydroxylamino and derivatives thereof, hydrazino and derivatives thereof, sulfinyl or a derivative thereof, or sulfonyl or a derivative thereof; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; or two of $R^A$ are taken together with the attached carbons to form an optionally substituted saturated, unsaturated, or aromatic carbocycle or heterocycle.

In another embodiment, described herein is a method as described above wherein the hydrazinopyridazine or fused hydrazinopyridazine is a compound of the formula

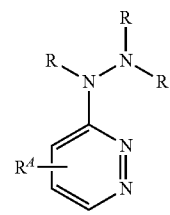

or a pharmaceutically acceptable salt thereof, wherein:

R is independently selected in each instance from hydrogen, acyl, or sulfonyl; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; and $R^A$ represents three substituents selected from the group consisting of hydrogen, halo, hydroxy and derivatives thereof, amino and derivatives thereof, thio and derivatives thereof, acyl, carboxylate or a derivative thereof, hydroxylamino and derivatives thereof, hydrazino and derivatives thereof, sulfinyl or a derivative thereof, or sulfonyl or a derivative thereof; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; or two of $R^A$ are taken together with the attached carbons to form an optionally substituted saturated, unsaturated, or aromatic carbocycle or heterocycle.

In another embodiment, described herein is a method as described above wherein $R^A$ represents three hydrogens.

In another embodiment, described herein is a method as described above wherein $R^A$ includes an optionally substituted benzo group.

In another embodiment, described herein is a method as described above wherein $R^A$ includes an optionally substituted fused piperidine.

In another embodiment, described herein is a method as described above wherein $R^A$ includes a hydrazino or derivative thereof.

In another embodiment, described herein is a method as described above wherein $R^A$ includes a hydrazino.

In another embodiment, described herein is a method as described above wherein $R^A$ includes amino or a derivative thereof.

In another embodiment, described herein is a method as described above wherein $R^A$ includes dialkylamino, where each alkyl is independently selected, and independently optionally substituted.

In another embodiment, described herein is a method as described above wherein each R is hydrogen.

In another embodiment, described herein is a method as described above wherein at least one R is acyl.

In another embodiment, described herein is a method as described above wherein at least one R is optionally substituted alkoxycarbonyl.

In another embodiment, described herein is a method as described above wherein the compound is selected from the group consisting of hydralazine, cadralazine, dihydralazine, endralazine, and combinations thereof.

In another embodiment, described herein is a use of one or more hydrazinopyridazines, fused hydrazinopyridazines, phenylethylhydrazines, or combinations for the treatment of pain.

In another embodiment, described herein is the use wherein the phenylethylhydrazine is a compound of the formula

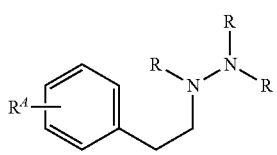

or a pharmaceutically acceptable salt thereof, wherein:
R is independently selected in each instance from hydrogen, acyl, or sulfonyl; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; and $R^A$ represents three substituents selected from the group consisting of hydrogen, halo, hydroxy and derivatives thereof, amino and derivatives thereof, thio and derivatives thereof, acyl, carboxylate or a derivative thereof, hydroxylamino and derivatives thereof, hydrazino and derivatives thereof, sulfinyl or a derivative thereof, or sulfonyl or a derivative thereof; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; or two of $R^A$ are taken together with the attached carbons to form an optionally substituted saturated, unsaturated, or aromatic carbocycle or heterocycle.

In another embodiment, described herein is any one of the preceding uses wherein the hydrazinopyridazine or fused hydrazinopyridazine is a compound of the formula

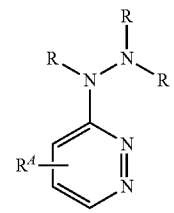

or a pharmaceutically acceptable salt thereof, wherein:
R is independently selected in each instance from hydrogen, acyl, or sulfonyl; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; and $R^A$ represents three substituents selected from the group consisting of hydrogen, halo, hydroxy and derivatives thereof, amino and derivatives thereof, thio and derivatives thereof, acyl, carboxylate or a derivative thereof, hydroxylamino and derivatives thereof, hydrazino and derivatives thereof, sulfinyl or a derivative thereof, or sulfonyl or a derivative thereof; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; or two of $R^A$ are taken together with the attached carbons to form an optionally substituted saturated, unsaturated, or aromatic carbocycle or heterocycle.

In another embodiment, described herein is any one of the preceding uses wherein $R^A$ represents three hydrogens.

In another embodiment, described herein is any one of the preceding uses wherein $R^A$ includes an optionally substituted benzo group.

In another embodiment, described herein is any one of the preceding uses wherein $R^A$ includes an optionally substituted fused piperidine.

In another embodiment, described herein is any one of the preceding uses wherein $R^A$ includes a hydrazino or derivative thereof.

In another embodiment, described herein is any one of the preceding uses wherein $R^A$ includes a hydrazino.

In another embodiment, described herein is any one of the preceding uses wherein $R^A$ includes amino or a derivative thereof.

In another embodiment, described herein is any one of the preceding uses wherein $R^A$ includes dialkylamino, where each alkyl is independently selected, and independently optionally substituted.

In another embodiment, described herein is any one of the preceding uses wherein each R is hydrogen.

In another embodiment, described herein is any one of the preceding uses wherein at least one R is acyl.

In another embodiment, described herein is any one of the preceding uses wherein at least one R is optionally substituted alkoxycarbonyl.

In another embodiment, described herein is any one of the preceding uses wherein the compounds is selected from the group consisting of hydralazine, cadralazine, dihydralazine, endralazine, and combinations thereof.

In another embodiment, described herein is a unit dosage form for treating multiple sclerosis, the unit dosage form comprising one or more hydrazinopyridazines, fused hydrazinopyridazines, phenylethylhydrazines, or combinations thereof.

In another embodiment, described herein is a unit dosage form as described above wherein the phenylethylhydrazine is a compound of the formula

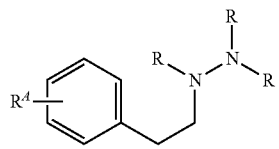

or a pharmaceutically acceptable salt thereof, wherein:

R is independently selected in each instance from hydrogen, acyl, or sulfonyl; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; and $R^A$ represents three substituents selected from the group consisting of hydrogen, halo, hydroxy and derivatives thereof, amino and derivatives thereof, thio and derivatives thereof, acyl, carboxylate or a derivative thereof, hydroxylamino and derivatives thereof, hydrazino and derivatives thereof, sulfinyl or a derivative thereof, or sulfonyl or a derivative thereof; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; or two of $R^A$ are taken together with the attached carbons to form an optionally substituted saturated, unsaturated, or aromatic carbocycle or heterocycle.

In another embodiment, described herein is a unit dosage form for treating multiple sclerosis, the unit dosage form comprising one or more hydrazinopyridazines, fused hydrazinopyridazines, or combinations thereof.

In another embodiment, described herein is a unit dosage form as described above wherein the hydrazinopyridazine or fused hydrazinopyridazine is a compound of the formula

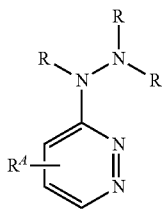

or a pharmaceutically acceptable salt thereof, wherein:

R is independently selected in each instance from hydrogen, acyl, or sulfonyl; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; and $R^A$ represents three substituents selected from the group consisting of hydrogen, halo, hydroxy and derivatives thereof, amino and derivatives thereof, thio and derivatives thereof, acyl, carboxylate or a derivative thereof, hydroxylamino and derivatives thereof, hydrazino and derivatives thereof, sulfinyl or a derivative thereof, or sulfonyl or a derivative thereof; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; or two of $R^A$ are taken together with the attached carbons to form an optionally substituted saturated, unsaturated, or aromatic carbocycle or heterocycle.

In another embodiment, the unit dosage form includes a compound as described above wherein $R^A$ represents three hydrogens.

In another embodiment, the unit dosage form includes a compound as described above wherein $R^A$ includes an optionally substituted benzo group.

In another embodiment, the unit dosage form includes a compound as described above wherein $R^A$ includes an optionally substituted fused piperidine.

In another embodiment, the unit dosage form includes a compound as described above wherein $R^A$ includes a hydrazino or derivative thereof.

In another embodiment, the unit dosage form includes a compound as described above wherein $R^A$ includes a hydrazino.

In another embodiment, the unit dosage form includes a compound as described above wherein $R^A$ includes amino or a derivative thereof.

In another embodiment, the unit dosage form includes a compound as described above wherein $R^A$ includes dialkylamino, where each alkyl is independently selected, and independently optionally substituted.

In another embodiment, the unit dosage form includes a compound as described above wherein each R is hydrogen.

In another embodiment, the unit dosage form includes a compound as described above wherein at least one R is acyl.

In another embodiment, the unit dosage form includes a compound as described above wherein at least one R is optionally substituted alkoxycarbonyl.

In another embodiment, the unit dosage form includes a compound as described above wherein the compound is selected from the group consisting of hydralazine, cadralazine, dihydralazine, endralazine, and combinations thereof.

In another embodiment, described herein is a unit dosage form as described above wherein the unit dosage form is a single or divided daily dose that sums to a daily amount of about 0.1 mg to about 100 mg of the compound.

In another embodiment, described herein is a unit dosage form as described above wherein the unit dosage form is a single or divided daily dose that sums to a daily amount of about 1 mg to about 100 mg of the compound.

In another embodiment, described herein is a unit dosage form as described above wherein the unit dosage form is a single or divided daily dose that sums to a daily amount of about 1 mg to about 75 mg of the compound.

In another embodiment, described herein is a unit dosage form as described above wherein the unit dosage form is a single or divided daily dose that sums to a daily amount of about 1 mg to about 50 mg of the compound.

In another embodiment, described herein is a unit dosage form as described above wherein the unit dosage form is a single or divided daily dose that sums to a daily amount of about 1 mg to about 40 mg of the compound.

In another embodiment, described herein is a unit dosage form as described above wherein the unit dosage form is a single or divided daily dose that sums to a daily amount of about 1 mg to about 30 mg of the compound.

In another embodiment, described herein is a unit dosage form as described above wherein the unit dosage form is a single or divided daily dose that sums to a daily amount of about 1 mg to about 25 mg of the compound.

In another embodiment, described herein is a unit dosage form as described above wherein the unit dosage form is a single or divided daily dose that sums to a daily amount of about 1 mg to about 20 mg of the compound.

In another embodiment, described herein is a unit dosage form as described above wherein the unit dosage form is a single or divided daily dose that sums to a daily amount of about 1 mg to about 15 mg of the compound.

In another embodiment, described herein is a unit dosage form as described above wherein the unit dosage form is a single or divided daily dose that sums to a daily amount of about 1 mg to about 10 mg of the compound.

In another embodiment, described herein is a unit dosage form as described above further comprising one or more carriers, diluents, or excipients, or a combination thereof.

In another embodiment, described herein is a method for treating a patient with pain, the method comprising the step of administering to the patient a therapeutically effective amount of a compound capable of blocking or decreasing the action of acrolein on TRPA1.

Other illustrative embodiments of the invention are described by way of the following enumerated clauses:

1. A method for treating pain in a patient, the method comprising the step of administering to the patient a therapeutically effective amount of one or more hydrazinopyridazines, fused hydrazinopyridazines, phenylethylhydrazines, or combinations thereof.

2. The method of clause 1 wherein the phenylethylhydrazine is a compound of the formula

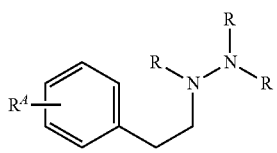

or a pharmaceutically acceptable salt thereof, wherein:

R is independently selected in each instance from hydrogen, acyl, or sulfonyl; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; and $R^A$ represents three substituents selected from the group consisting of hydrogen, halo, hydroxy and derivatives thereof, amino and derivatives thereof, thio and derivatives thereof, acyl, carboxylate or a derivative thereof, hydroxylamino and derivatives thereof, hydrazino and derivatives thereof, sulfinyl or a derivative thereof, or sulfonyl or a derivative thereof; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; or two of $R^A$ are taken together with the attached carbons to form an optionally substituted saturated, unsaturated, or aromatic carbocycle or heterocycle.

3. The method of clause 1 or 2 wherein the hydrazinopyridazine or fused hydrazinopyridazine is a compound of the formula

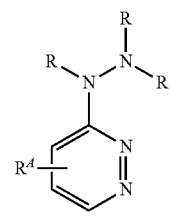

or a pharmaceutically acceptable salt thereof, wherein:

R is independently selected in each instance from hydrogen, acyl, or sulfonyl; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; and $R^A$ represents three substituents selected from the group consisting of hydrogen, halo, hydroxy and derivatives thereof, amino and derivatives thereof, thio and derivatives thereof, acyl, carboxylate or a derivative thereof, hydroxylamino and derivatives thereof, hydrazino and derivatives thereof, sulfinyl or a derivative thereof, or sulfonyl or a derivative thereof; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; or two of $R^A$ are taken together with the attached carbons to form an optionally substituted saturated, unsaturated, or aromatic carbocycle or heterocycle.

3a. The method of clause 1 or 2 wherein the hydrazinopyridazine or fused hydrazinopyridazine is a compound of the formula

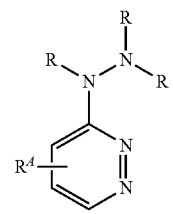

or a pharmaceutically acceptable salt thereof, wherein:

R is independently selected in each instance from hydrogen, acyl, or sulfonyl; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; or two R are taked together with the attached nitrogen to form a hydrazone; and $R^A$ represents three substituents selected from the group consisting of hydrogen, halo, hydroxy and derivatives thereof, amino and derivatives thereof, thio and derivatives thereof, acyl, carboxylate or a derivative thereof, hydroxylamino and derivatives thereof, hydrazino and derivatives thereof, sulfinyl or a derivative thereof, or sulfonyl or a derivative thereof; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; or two of $R^A$ are taken together with the attached carbons to form an optionally substituted saturated, unsaturated, or aromatic carbocycle or heterocycle.

3b. The method clause of 3a wherein the hydrazone is an alkylidene hydrazone.

3b. The method clause of 3a or 3b wherein the hydrazone is an alkylidene is 4-methyl-pent-3-ene-2,2-yl.

4. The method of any one of the preceding clauses wherein $R^4$ represents three hydrogens.

5. The method of any one of the preceding clauses wherein $R^4$ includes an optionally substituted benzo group.

6. The method of any one of the preceding clauses wherein $R^4$ is a benzo group.

7. The method of any one of clauses 1 to 3 wherein $R^4$ includes an optionally substituted fused piperidine.

8. The method of any one of the preceding clauses wherein $R^4$ includes a fused N-benzoyl piperidine.

9. The method of any one of the preceding clauses wherein $R^4$ includes a hydrazino or derivative thereof.

10. The method of any one of the preceding clauses wherein $R^4$ includes a hydrazino.

11. The method of any one of the preceding clauses wherein $R^4$ is hydrazino.

12. The method of any one of the preceding clauses wherein $R^4$ includes amino or a derivative thereof.

13. The method of any one of the preceding clauses wherein $R^4$ includes dialkylamino, where each alkyl is independently selected, and independently optionally substituted.

14. The method of any one of the preceding clauses wherein $R^4$ is ethyl(2-hydroxypropyl)amino, where each alkyl is independently selected, and independently optionally substituted.

16. The method of any one of the preceding clauses wherein each R is hydrogen.

17. The method of any one of the preceding clauses wherein at least one R is acyl.

18. The method of any the preceding clauses wherein at least one R is optionally substituted alkoxycarbonyl.

19. The method of any the preceding clauses wherein one R is ethyloxycarbonyl, and the remaining R are each hydrogen.

20. The method of any the preceding clauses wherein the compound is selected from the group consisting of hydralazine, cadralazine, dihydralazine, endralazine, pildralazine, todralazine, and budralazine, and combinations thereof.

20a. The method of any the preceding clauses wherein the compound is selected from the group consisting of hydralazine, cadralazine, dihydralazine, endralazine, and combinations thereof.

21. A unit dosage form for treating pain, the unit dosage form comprising a therapeutically effective amount of one or more hydrazinopyridazines, fused hydrazinopyridazines, phenylethylhydrazines, or combinations thereof.

22. The unit dosage form of clause 21 wherein the phenylethylhydrazine is a compound of the formula

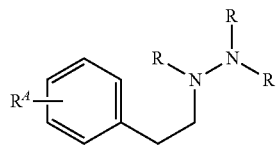

or a pharmaceutically acceptable salt thereof, wherein:

R is independently selected in each instance from hydrogen, acyl, or sulfonyl; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; and $R^4$ represents three substituents selected from the group consisting of hydrogen, halo, hydroxy and derivatives thereof, amino and derivatives thereof, thio and derivatives thereof, acyl, carboxylate or a derivative thereof, hydroxylamino and derivatives thereof, hydrazino and derivatives thereof, sulfinyl or a derivative thereof, or sulfonyl or a derivative thereof; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; or two of $R^4$ are taken together with the attached carbons to form an optionally substituted saturated, unsaturated, or aromatic carbocycle or heterocycle.

22a. The unit dosage form of clause 21 wherein the phenylethylhydrazine is a compound of the formula

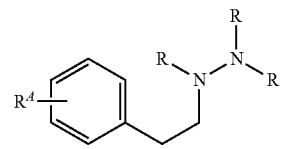

or a pharmaceutically acceptable salt thereof, wherein:

R is independently selected in each instance from hydrogen, acyl, or sulfonyl; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; or two R are taked together with the attached nitrogen to form a hydrazone; and $R^4$ represents three substituents selected from the group consisting of hydrogen, halo, hydroxy and derivatives thereof, amino and derivatives thereof, thio and derivatives thereof, acyl, carboxylate or a derivative thereof, hydroxylamino and derivatives thereof, hydrazino and derivatives thereof, sulfinyl or a derivative thereof, or sulfonyl or a derivative thereof; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; or two of $R^4$ are taken together with the attached carbons to form an optionally substituted saturated, unsaturated, or aromatic carbocycle or heterocycle.

22b. The unit dosage form of clause of 3a wherein the hydrazone is an alkylidene hydrazone.

22b. The unit dosage form clause of 3a or 3b wherein the hydrazone is an alkylidene is 4-methyl-pent-3-ene-2,2-yl.

23. A unit dosage form for treating pain, the unit dosage form comprising a therapeutically effective amount of one or more hydrazinopyridazines, fused hydrazinopyridazines, or combinations thereof.

24. The unit dosage form of clause 23 wherein the hydrazinopyridazine or fused hydrazinopyridazine is a compound of the formula

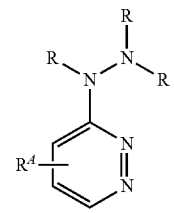

or a pharmaceutically acceptable salt thereof, wherein:

R is independently selected in each instance from hydrogen, acyl, or sulfonyl; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; and $R^A$ represents three substituents selected from the group consisting of hydrogen, halo, hydroxy and derivatives thereof, amino and derivatives thereof, thio and derivatives thereof, acyl, carboxylate or a derivative thereof, hydroxylamino and derivatives thereof, hydrazino and derivatives thereof, sulfinyl or a derivative thereof, or sulfonyl or a derivative thereof; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; or two of $R^A$ are taken together with the attached carbons to form an optionally substituted saturated, unsaturated, or aromatic carbocycle or heterocycle.

25. The unit dosage form of any one of the preceding clauses wherein $R^A$ represents three hydrogens.

26. The unit dosage form of any one of the preceding clauses wherein $R^A$ includes an optionally substituted benzo group.

27. The unit dosage form of any one of the preceding clauses wherein $R^A$ is a benzo group.

28. The unit dosage form of any one of the preceding clauses wherein $R^A$ includes an optionally substituted fused piperidine.

29. The unit dosage form of any one of the preceding clauses wherein $R^A$ includes a fused N-benzoyl piperidine.

30. The unit dosage form of any one of the preceding clauses wherein $R^A$ includes a hydrazino or derivative thereof.

31. The unit dosage form of any one of the preceding clauses wherein $R^A$ includes a hydrazino.

32. The unit dosage form of any one of the preceding clauses wherein $R^A$ is hydrazino.

33. The unit dosage form of any one of the preceding clauses wherein $R^A$ includes amino or a derivative thereof.

34. The unit dosage form of any one of the preceding clauses wherein $R^A$ includes dialkylamino, where each alkyl is independently selected, and independently optionally substituted.

35. The unit dosage form of any one of the preceding clauses wherein each R is hydrogen.

36. The unit dosage form of any one of the preceding clauses wherein $R^A$ is ethyl(2-hydroxypropyl)amino, where each alkyl is independently selected, and independently optionally substituted.

37. The unit dosage form of any one of the preceding clauses wherein at least one R is acyl.

38. The unit dosage form of any one of the preceding clauses wherein at least one R is optionally substituted alkoxycarbonyl.

39. The unit dosage form of any one of the preceding clauses wherein one R is ethyloxycarbonyl, and the remaining R are each hydrogen.

40. The unit dosage form of any one of the preceding clauses wherein the compound is selected from the group consisting of hydralazine, cadralazine, dihydralazine, endralazine, pildralazine, todralazine, and budralazine, and combinations thereof.

40a. The unit dosage form of any one of the preceding clauses wherein the compound is selected from the group consisting of hydralazine, cadralazine, dihydralazine, endralazine, and combinations thereof.

41. The unit dosage form of any one of the preceding clauses wherein the unit dosage form is a single or divided daily dose that sums to a daily amount of about 1 mg to about 50 mg of the compound.

42. The unit dosage form of any one of the preceding clauses wherein the unit dosage form is a single or divided daily dose that sums to a daily amount of about 1 mg to about 40 mg of the compound.

43. The unit dosage form of any one of the preceding clauses wherein the unit dosage form is a single or divided daily dose that sums to a daily amount of about 1 mg to about 30 mg of the compound.

44. The unit dosage form of any one of the preceding clauses wherein the unit dosage form is a single or divided daily dose that sums to a daily amount of about 1 mg to about 25 mg of the compound.

45. The unit dosage form of any one of the preceding clauses wherein the unit dosage form is a single or divided daily dose that sums to a daily amount of about 1 mg to about 20 mg of the compound.

46. The unit dosage form of any one of the preceding clauses wherein the unit dosage form is a single or divided daily dose that sums to a daily amount of about 1 mg to about 15 mg of the compound.

47. The unit dosage form of any one of the preceding clauses wherein the unit dosage form is a single or divided daily dose that sums to a daily amount of about 1 mg to about 10 mg of the compound.

48. The unit dosage form of any one of the preceding clauses further comprising one or more carriers, diluents, or excipients, or a combination thereof.

49. The method or unit dosage form of any one of the preceding clauses wherein the pain is allodynia.

50. The method or unit dosage form of any one of clauses the preceding clauses wherein the pain is a neuropathy.

51. The method or unit dosage form of any one of the preceding clauses wherein the pain is associated with multiple sclerosis.

52. The method or unit dosage form of any one of the preceding clauses wherein the pain is associated with diabetes.

53. The method or unit dosage form of any one of the preceding clauses wherein the pain is associated with neuronal injury.

54. The method or unit dosage form of any one of the preceding clauses wherein the pain is associated with spinal cord injury. In each of the foregoing and following embodiments, it is to be understood that the formulae include and represent not only all pharmaceutically acceptable salts of the compounds, but also include any and all hydrates and/or solvates of the compound formulae. It is appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non crystalline and/or amorphous forms of the compounds.

As used herein, the terms hydrazinopyridazines, fused hydrazinopyridazines, and phenylethylhydrazines generally refers to the compounds described herein and analogs and derivatives thereof, but are not limited to those compounds.

Other compounds that are hydrazinopyridazines, fused hydrazinopyridazines, and phenylethylhydrazines are also useful in the methods, uses, formulations, and unit dosage forms described herein. It is also to be understood that in each of the foregoing, any corresponding pharmaceutically acceptable salt is also included in the illustrative embodiments described herein.

Illustrative derivatives include, but are not limited to, both those compounds that may be synthetically prepared from the compounds described herein, as well as those compounds that may be prepared in a similar way as those described herein, but differing in the selection of starting materials. For example, it is to be understood that derivatives of those compounds also include the compounds having for example different functional groups on aromatic rings than those explicitly set forth in the compound genera described herein. In addition, it is to be understood that derivatives of those compounds also include the compounds having those same or different functional groups at different positions on the aromatic ring.

It is to be understood that such derivatives may include prodrugs of the compounds described herein, compounds described herein that include one or more protection or protecting groups, including compounds that are used in the preparation of other compounds described herein.

Illustrative analogs include, but are not limited to, those compounds that share functional and in some cases structural similarity to those compounds described herein. For example, described herein are compounds that include a benzopyridazine ring system. Illustrative analogs include, but are not limited to, the corresponding ring expanded or ring contracted compounds, and the like. Other illustrative analogs include, but are not limited to, the corresponding ring systems that include additional heteroatoms, or where the ring fusion is made at a different pair of atoms, and the like.

In addition, as used herein the terms hydrazinopyridazines, fused hydrazinopyridazines, and phenylethylhydrazines also refer to prodrug derivatives of the compounds described herein, and including prodrugs of the various analogs and derivatives thereof. In addition, as used herein, the terms hydrazinopyridazines, fused hydrazinopyridazines, and phenylethylhydrazines also refer to both the amorphous as well as any and all morphological forms of each of the compounds described herein. In addition, as used herein, the terms hydrazinopyridazines, fused hydrazinopyridazines, and phenylethylhydrazines also refer to any and all hydrates, or other solvates, of the compounds described herein.

It is to be understood that each of the foregoing embodiments may be combined in chemically relevant ways to generate subsets of the embodiments described herein. Accordingly, it is to be further understood that all such subsets are also illustrative embodiments of the invention described herein. For example, in another embodiment, when each R is hydrogen, $R^A$ includes an optionally substituted benzo group; or when at least one R is acyl, $R^A$ includes a hydrazine; or when at least one R is acyl, $R^A$ includes an optionally substituted benzo group; and the like.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may be include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopenyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, heteroarylamino, heteroarylalkylamino, heteroarylalkenylamino, heteroarylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, heteroaryloxy, heteroarylalkyloxy, heteroarylalkenyloxy, heteroarylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, heteroarylthio, heteroarylalkylthio, heteroarylalkenylthio, heteroarylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, acylcarbonyl, and the like, each of which is optionally substituted.

As used herein, the term "carbonyl and derivatives thereof" includes the group C(O), C(S), C(NH) and substituted amino derivatives thereof.

As used herein, the term "carboxylate and derivatives thereof" includes the group $CO_2H$ and salts thereof, and esters and amides thereof, and CN.

As used herein, the term "sulfinyl or a derivative thereof" includes $SO_2H$ and salts thereof, and esters and amides thereof.

As used herein, the term "sulfonyl or a derivative thereof" includes $SO_3H$ and salts thereof, and esters and amides thereof.

As used herein, the term "hydroxylamino and derivatives thereof" includes NHOH, and alkyloxylNH alkenyloxylNH alkynyloxylNH heteroalkyloxylNH heteroalkenyloxylNH heteroalkynyloxylNH cycloalkyloxylNH cycloalkenyloxylNH cycloheteroalkyloxylNH cycloheteroalkenyloxylNH aryloxylNH arylalkyloxylNH arylalkenyloxylNH arylalkynyloxylNH heteroaryloxylNH heteroarylalkyloxylNH heteroarylalkenyloxylNH heteroarylalkynyloxylNH acyloxy, and the like, each of which is optionally substituted.

As used herein, the term "hydrazino and derivatives thereof" includes alkylNHNH, alkenylNHNH, alkynylNHNH, heteroalkylNHNH, heteroalkenylNHNH, heteroalkynylNHNH, cycloalkylNHNH, cycloalkenylNHNH, cycloheteroalkylNHNH, cycloheteroalkenylNHNH, arylNHNH, arylalkylNHNH, arylalkenylNHNH, arylalkynylNHNH, heteroarylNHNH, heteroarylalkylNHNH, heteroarylalkenylNHNH, heteroarylalkynylNHNH, acylNHNH, and the like, each of which is optionally substituted.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

Illustrative substituents include, but are not limited to, a radical $—(CH_2)_x Z^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, and nitro; or $Z^X$ is selected from —$CO_2R^4$ and —$CONR^5R^6$, where $R^4$, $R^5$, and $R^6$ are each independently selected in each occurrence from hydrogen, $C_1$-$C_6$ alkyl, aryl-$C_1$-$C_6$ alkyl, and heteroaryl-$C_1$-$C_6$ alkyl.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —$CO_2H$, —$NR_2$. Illustrative prodrugs include but are not limited to carboxylate esters where the group is alkyl, aryl, arylalkyl, heteroaryl, heteroarylalkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, ($C_3$-$C_{20}$)alkanoyl; halo-($C_3$-$C_{20}$)alkanoyl; ($C_3$-$C_{20}$)alkenoyl; ($C_4$-$C_7$)cycloalkanoyl; ($C_3$-$C_6$)-cycloalkyl($C_2$-$C_{16}$)alkanoyl; optionally substituted aroyl, such as unsubstituted aroyl or aroyl substituted by 1 to 3 substituents selected from the group consisting of halogen, cyano, trifluoromethanesulphonyloxy, ($C_1$-$C_3$)alkyl and ($C_1$-$C_3$)alkoxy, each of which is optionally further substituted with one or more of 1 to 3 halogen atoms; optionally substituted aryl($C_2$-$C_{16}$)alkanoyl and optionally substituted heteroaryl($C_2$-$C_{16}$)alkanoyl, such as the aryl or heteroaryl radical being unsubstituted or substituted by 1 to 3 substituents selected from the group consisting of halogen, ($C_1$-$C_3$)alkyl and ($C_1$-$C_3$)alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, ($C_1$-$C_3$)alkyl, and ($C_1$-$C_3$)alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

As used herein "treating pain", "pain treatment", and the like mean alleviating or ameliorating one or more symptoms associated with pain or improving one or more etiological factors associated with pain. The phrases "treating pain", "pain treatment", and the like further include prophylacetic treatment of the subject to prevent the onset of the sensation of pain. Thus, treatment of pain can include a complete and/or partial abolition of the sensation of pain. Illustratively, treatment can include any reduction in the sensation and/or symptoms of pain including reducing the intensity and/or unpleasantness of the perceived pain.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a cotherapy.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, ($21^{st}$ ed., 2005)).

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and vehicles.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

Illustrative routes of oral administration include tablets, capsules, elixirs, syrups, and the like. Illustrative routes for parenteral administration include intravenous, intraarterial, intraperitoneal, epidurial, intraurethral, intrasternal, intramuscular, intrathecal, and subcutaneous, as well as any other art recognized route of parenteral administration.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

Depending upon the disease as described herein, the route of administration and/or whether the compounds and/or compositions are administered locally or systemically, a wide range of permissible dosages are contemplated herein, including doses falling in the range from about 1 µg/kg to about 1 g/kg. The dosages may be single or divided, and may administered according to a wide variety of protocols, including q.d., b.i.d., t.i.d., or even every other day, once a week, once a month, once a quarter, and the like. In each of these cases it is understood that the total daily, weekly, month, or quarterly dose corresponds to the therapeutically effective amounts described herein.

In addition to the foregoing illustrative dosages and dosing protocols, it is to be understood that an effective amount of any one or a mixture of the compounds described herein can be readily determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

In making the pharmaceutical compositions of the compounds described herein, a therapeutically effective amount of one or more compounds in any of the various forms described herein may be mixed with one or more excipients, diluted by one or more excipients, or enclosed within such a carrier which can be in the form of a capsule, sachet, paper, or other container. Excipients may serve as a diluent, and can be solid, semi-solid, or liquid materials, which act as a vehicle, carrier or medium for the active ingredient. Thus, the formulation compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. The compositions may contain anywhere from about 0.1% to about 99.9% active ingredients, depending upon the selected dose and dosage form.

The effective use of the compounds, compositions, and methods described herein for treating or ameliorating one or more effects of pain using one or more compounds described herein may be based upon animal models, such as murine, canine, porcine, and non-human primate animal models of disease. For example, it is understood that MS in humans is often accompanied by chronic pain, which may be elicited in animal models, such as mice, and other surrogate test animals. In particular the mouse EAE model may be used to evaluate the methods of treatment and the pharmaceutical compositions described herein to determine the therapeutically effective amounts described herein. In addition, other animal models of neuropathic pain and injury, such as spinal cord injury models, may be used to evaluate the methods of treatment and the pharmaceutical compositions described herein to determine the therapeutically effective amounts described herein.

The following examples further illustrate specific embodiments of the invention; however, the following illustrative examples should not be interpreted in any way to are to limit invention.

EXAMPLES

Example 1

Detection of acrolein-Lysine adducts by immunoblotting. Acrolein-lysine adducts in the tissue homogenate from test animals is measured using a Bio-Dot SF Microfiltration Apparatus (Bio-Rad, Hercules, Calif., USA), as previously described (Luo et al., 2005a; Shao et al., 2006; Hamann et al., 2008a). Briefly, the tissue is homogenized with TritonX-100 (3%), and the following anti-proteases is added: 2 mmol/L pefabloc, 15 lmol/L pepstatin A, 20 1 g/mL aprotinin, and 25 1 g/mL leupeptin. The solution is centrifuged to pellet large pieces of tissue and the supernatant is stored at −80° C. until transferred to a nitrocellulose membrane. The membrane is blocked for 1 h in blocking buffer (0.2% casein and 0.1% Tween 20 in PBS) and transferred to 1:1000 polyclonal rabbit anti-acrolein (in blocking buffer with 2% goat serum and 0.025% sodium azide) (Novus Biologicals) for 18 h at 4° C. The membrane is washed in blocking buffer and then transferred to 1:10000 alkaline phosphatase conjugated goat anti-rabbit IgG, then washed in blocking buffer followed by 0.1% Tween 20 in Tris-buffered saline. The membrane is exposed to Bio-Rad Immuno-Star Substrate (Bio-Rad) and visualized by chemiluminescence.

The optical density of bands are evaluated using Image J (NIH) and statistical comparison is performed with SAS 9.2 (SAS institute). Specifically, equal areas of each individual immunoblotted band of both anti-acrolein and anti-actin samples are selected and corresponding optical densities are obtained using Image J. The optical densities obtained from the anti-acrolein samples are standardized by their corresponding anti-actin samples before proceeding to statistical analysis. A Bicinchoninic acid (BCA) protein assay is also performed before the experiment to ensure equal loading of the samples.

Example 2

Spinal contusion injury. Sprague Dawley rats are subjected to a spinal contusion injury according to the procedure described by Basso et al., Graded histological and locomotor outcomes after spinal cord contusion using the NYU weight-drop device versus transaction, Exp Neurol. 139:244-256 (1996). After 20 weeks, the animals are divided into untreated injury and treated injury groups, each of which is compared to an uninjured control.

Example 3

Elevation of acrolein and its inhibition in rat spinal cord in vivo 24 hours follow contusion injury. Concentrations of acrolein-protein adducts are measured in spinal cords of control rats receiving sham injuries, rats with moderate and severe contusions, and rats receiving severe contusion injuries and hydralazine treatment. Hydralazine is applied systemically through a single intraperitoneal injection at a dose of 5 mg/kg body weight. The relative densities of samples in the upper part of the figure are converted to concentrations based on standard curves. Quantitative analysis (n=4 in all cases) indicates that both moderate and severe contusion injuries produced graded and significant elevation of acrolein. In addition, hydralazine significantly reduced acrolein levels in severe contusion injuries. See FIG. 1.

Example 4

Test compound treatment. A solution of test compound, such as hydralazine hydrochloride (Sigma), is prepared with phosphate buffered saline. The solution is sterilized through a filter and stored at 4° C. Test compound, such as hydralazine, is administered daily (0.05-5 mg/kg) by intraperitoneal injection. Untreated animals are administered saline vehicle intraperitoneally. Blood pressures are monitored using a CODA 2 system (Kent Scientific Corp.).

Example 5

Mechanical allodynia evaluation. Sprague Dawley rats models of spinal contusion injury are divided into untreated injury and treated injury groups. The untreated injury groups are injected daily with vehicle as described herein. The treated injury groups are injected daily with test compound as described herein. Uninjured controls, untreated injury groups, and treated injury groups are evaluated for pain according to the procedure described by Choi et al., Behavioral signs of ongoing pain and cold allodynia in a rat model of neuropathic pain, Pain 59:369-376 (1994).

Example 6

Cold allodynia evaluation. Sprague Dawley rats models of spinal contusion injury are divided into untreated injury and treated injury groups. The untreated injury groups are injected daily with vehicle as described herein. The treated injury groups are injected daily with test compound as described herein. Uninjured controls, untreated injury groups, and treated injury groups are evaluated for pain according to the procedure described by Choi et al., Behavioral signs of ongoing pain and cold allodynia in a rat model of neuropathic pain, Pain 59:369-376 (1994).

Example 7

Figure 2:
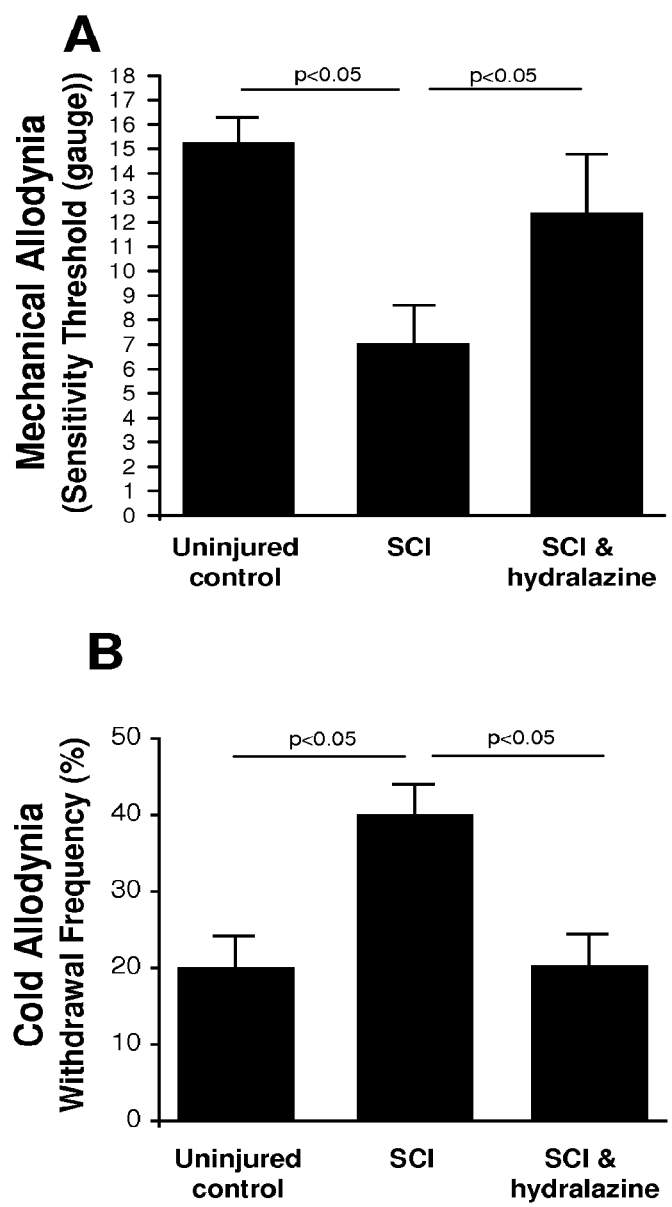
FIG. 2. Mechanical and cold allodynia in chronic spinal cord injury treatment with hydralazine. Panel A) Mechanical allodynia increased significantly in chronic spinal cord injury (5 months). Injection of a single dose of hydralazine (intraperitoneal) at 5 mg/kg body weight reduced the mechanical allodynia to a level that was not significantly different compared to uninjured control. Mechanical allodynia showed improvement within 2 days after the injection. Panel B) Cold allodynia was increased significantly in chronic spinal cord injury (5 months). Injection of a single dose of hydralazine (intraperitoneal) at 5 mg/kg body weight reduced cold allodynia to a level that was comparable to uninjured control. Cold-induced pain showed improvement within 2 hours after the injection. The efficacy of the treatment lasted at least 10 days (see FIG. 2, panel B)
Figure 3:
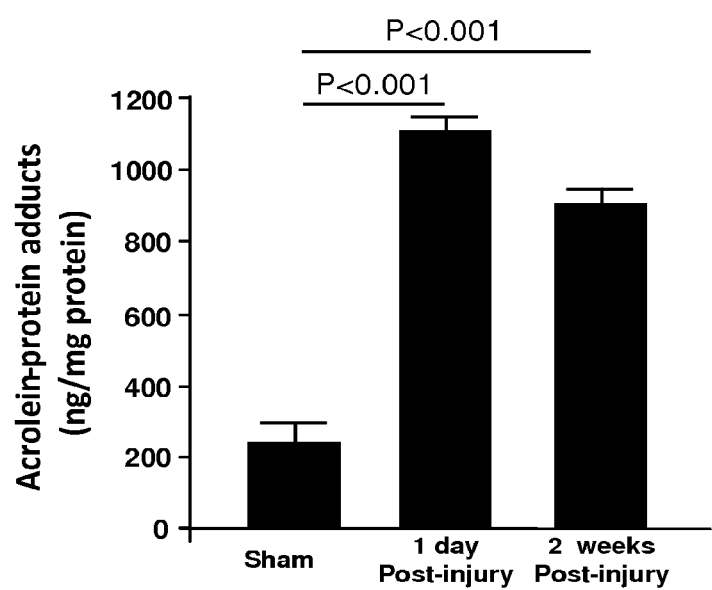
FIG. 3. Persistent elevation of acrolein following SCI in rats. This figure indicates that following rat SCI, levels of acrolein remain elevated at least 2 weeks after trauma. Neuropathic pain is well established 2 weeks after SCI, this data supports a contribution of acrolein to neuropathic pain post SCI. Error bar: SD. N=6 in all cases.
Figure 4A:
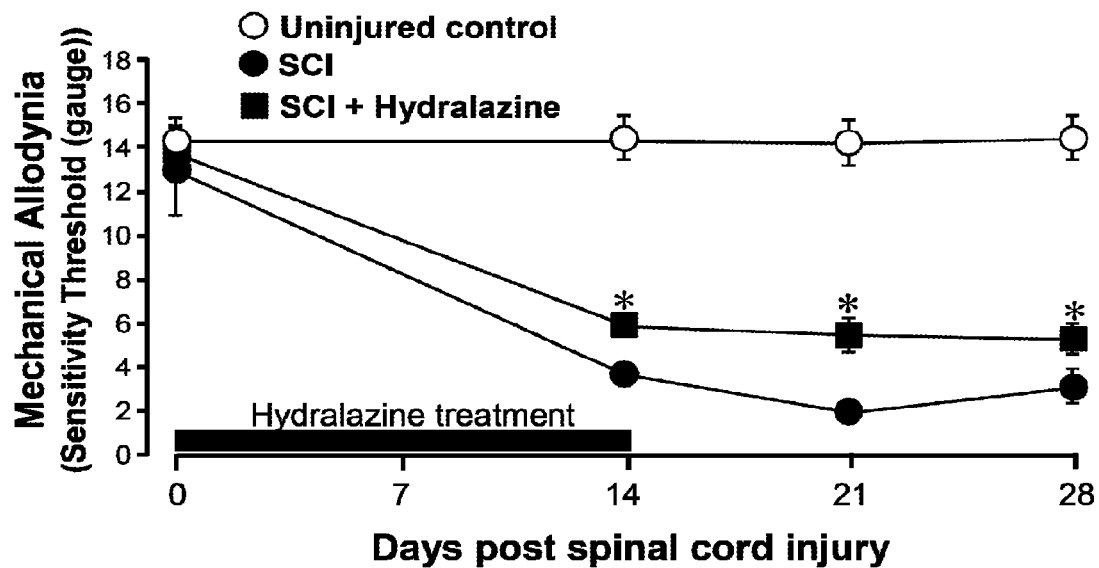
FIGS. 4A to 4C. Hydralazine alleviates acute neuropathic pain following SCI in rats. These three figures indicate that hydralazine, a known acrolein scavenger, when applied daily for two weeks (5 mg/kg body weight) attenuated mechanical, thermal, and cold neuropathic pain following rat SCI. N=4-8 in all cases. Error bar: SD, * indicates p<0.05 when compared to SCI.
Figure 4B:
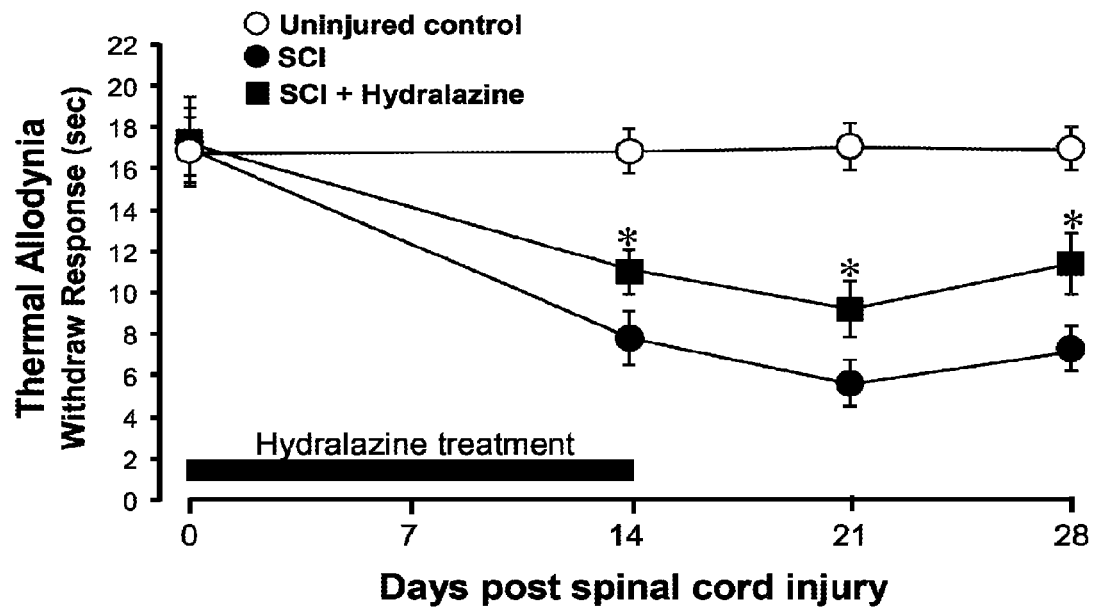
Figure 4C:
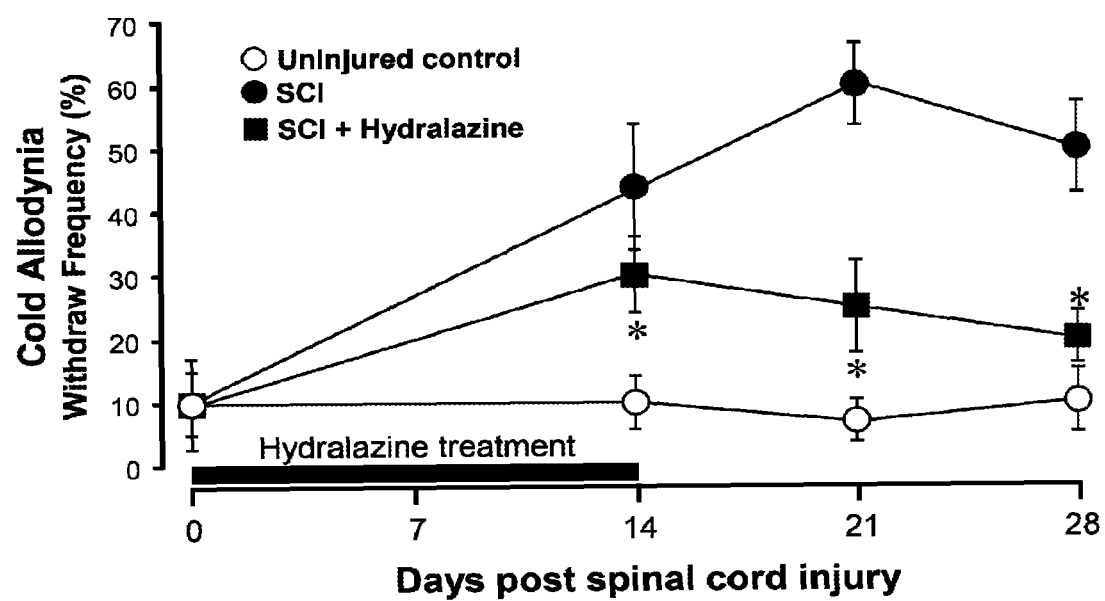

Mechanical and cold allodynia in chronic spinal cord injury treatment with hydralazine. A) Mechanical allodynia increased significantly in chronic spinal cord injury (5 months). Injection of a single dose of hydralazine (intraperitoneal) at 5 mg/kg body weight significantly reduced the mechanical allodynia to a level that was not significantly different compared to uninjured control. It was observed that mechanical allodynia showed improvement within 2 days after the injection. The efficacy of the treatment lasted at least 10 days (see FIG. 2, panel A). B) Cold-induced pathological pain (cold allodynia) was increased significantly in chronic spinal cord injury (5 months). Injection of a single dose of hydralazine (intraperitoneal) at 5 mg/kg body weight significantly reduced cold allodynia to a level that was comparable to uninjured control. It was observed that cold-induced pain showed improvement within 2 hours after the injection. The efficacy of the treatment lasted at least 10 days (see FIG. 2, panel B).

Example 8

Induction of EAE and chronic associated pain. C57BL/6 female mice (8 weeks old) are purchased from Harlan Laboratories and maintained in the lab animal housing facilities. These studies are performed in compliance with the Purdue Animal Care and Use Committee protocol guidelines at Purdue University, West Lafayette, Ind. Nine-twelve week old mice are subcutaneously injected with 0.1 mL $MOG_{35-55}$/CFA emulsion (EK-0115, Hooke Laboratories) in the neck and lower back (total of 0.2 mL). Within two hours of the injection, 0.1 mL pertussis toxin (EK-0115, Hooke Laboratories) is administered intraperitoneally. A second dose of pertussis toxin of the same volume is given 22-26 hours later. The behavioral performance is assessed using a well established 5-point behavioral scoring system (Kalyvas and David, 2004). The animals are placed on a metal grate and their walking ability is recorded. The scoring system is as follows: 0—no deficit; 1—limp tail only; 2—hind limb paresis but without leg dragging; 3—partial hind limb weakness with one or both legs dragging; 4—complete hind limb paralysis; 5—moribund, paralysis in hind limbs and possibly in one forelimb. Following the development of symptoms, test animals are evaluated for pain in control, untreated disease, and treated disease groups, as described herein.

The following publications, and each additional publication cited herein, are incorporated herein by reference in their entirety.

1. Adams J D, Jr., Klaidman L K (1993) Acrolein-induced oxygen radical formation. Free Radical Biology & Medicine 15:187-193.
2. Burcham P C, Pyke S M (2006) Hydralazine inhibits rapid acrolein-induced protein oligomerization: role of aldehyde scavenging and adduct trapping in cross-link blocking and cytoprotection. Mol Pharmacol 69:1056-1065.
3. Burcham P C, Kerr P G, Fontaine F (2000) The antihypertensive hydralazine is an efficient scavenger of acrolein. Redox Rep 5:47-49.
4. Burcham P C, Kaminskas L M, Fontaine F R, Petersen D R, Pyke S M (2002) Aldehyde-sequestering drugs: tools for studying protein damage by lipid peroxidation products. Toxicology 181-182:229-236.
5. Burcham P C, Fontaine F R, Kaminskas L M, Petersen D R, Pyke S M (2004) Protein adduct-trapping by hydrazinophthalazine drugs: mechanisms of cytoprotection against acrolein-mediated toxicity. Mol Pharmacol 65:655-664.
6. Compston A, Coles A (2008) Multiple sclerosis. Lancet 372:1502-1517.
7. Esterbauer H, Schaur R J, Zollner H (1991) Chemistry and biochemistry of 4-hydroxynonenal, malonaldehyde and related aldehydes. Free Radical Biology & Medicine 11:81-128.
8. Ghilarducci D P, Tjeerdema R S (1995) Fate and effects of acrolein. Rev Environ Contam Toxicol 144:95-146.
9. Gilgun-Sherki Y, Melamed E, Offen D (2004) The role of oxidative stress in the pathogenesis of multiple sclerosis: the need for effective antioxidant therapy. J Neurol 251: 261-268.
10. Gold R, Linington C, Lassmann H (2006) Understanding pathogenesis and therapy of multiple sclerosis via animal models: 70 years of merits and culprits in experimental autoimmune encephalomyelitis research. Brain 129:1953-1971.
11. Halliwell B, Gutteridge J M C (1999) Free radicals in biology and medicine. Oxford: Oxford University Press.
12. Hamann K, Shi R (2009) Acrolein scavenging: a potential novel mechanism of attenuating oxidative stress following spinal cord injury. J Neurochem 111:1348-1356.
13. Hamann K, Nehrt G, Ouyang H, Duerstock B, Shi R (2008a) Hydralazine inhibits compression and acrolein-mediated injuries in ex vivo spinal cord. J Neurochem 104:708-718.
14. Hamann K, Durkes A, Ouyang H, Uchida K, Pond A, Shi R (2008b) Critical role of acrolein in secondary injury following ex vivo spinal cord trauma. J Neurochem 107:712-721.
15. Kalyvas A, David S (2004) Cytosolic phospholipase A2 plays a key role in the pathogenesis of multiple sclerosis-like disease. Neuron 41:323-335.
16. Kaminskas L M, Pyke S M, Burcham P C (2004a) Reactivity of hydrazinophthalazine drugs with the lipid peroxidation products acrolein and crotonaldehyde. Org Biomol Chem 2:2578-2584.
17. Kaminskas L M, Pyke S M, Burcham P C (2004b) Strong protein adduct trapping accompanies abolition of acrolein-mediated hepatotoxicity by hydralazine in mice. J Pharmacol Exp Ther 310:1003-1010.
18. Kehrer J P, Biswal S S (2000) The molecular effects of acrolein. Toxicological Sciences 57:6-15.
19. Liu-Snyder P, McNally H, Shi R, Borgens R B (2006) Acrolein-mediated mechanisms of neuronal death. J Neurosci Res 84:209-218.
20. Lovell M A, Xie C, Markesbery W R (2001) Acrolein is increased in Alzheimer's disease brain and is toxic to primary hippocampal cultures. Neurobiology of Aging 22:187-194.
21. Luo J, Shi R (2004) Acrolein induces axolemmal disruption, oxidative stress, and mitochondrial impairment in spinal cord tissue. Neurochemistry International 44:475-486.
22. Luo J, Shi R (2005) Acrolein induces oxidative stress in brain mitochondria. Neurochem Int 46:243-252.
23. Luo J, Uchida K, Shi R (2005a) Accumulation of acrolein-protein adducts after traumatic spinal cord injury. Neurochem Res 30:291-295.
24. Luo J, Robinson J P, Shi R (2005b) Acrolein-induced cell death in PC12 cells: role of mitochondria-mediated oxidative stress. Neurochem Int 47:449-457.

25. Montine T J, Neely M D, Quinn J F, Beal M F, Markesbery W R, Roberts L J, Morrow J D (2002) Lipid peroxidation in aging brain and Alzheimer's disease. Free Radic Biol Med 33:620-626.
26. Morell P, Quarles R H (1999) In: Basic Neurochemistry: Molecular, Cellular, and Medical Aspects (Siegel G J, Agranoff B W, Alberts R W, Molinoff P B, eds). Philadelphia: Lippincott Williams & Wilkins.
27. Shao B, O'Brien K D, McDonald T O, Fu X, Oram J F, Uchida K, Heinecke J W (2005a) Acrolein modifies apolipoprotein A-I in the human artery wall. Ann NY Acad Sci 1043:396-403.
28. Shao B, Fu X, McDonald T O, Green P S, Uchida K, O'Brien K D, Oram J F, Heinecke J W (2005b) Acrolein impairs ATP binding cassette transporter A1-dependent cholesterol export from cells through site-specific modification of apolipoprotein A-I. J Biol Chem 280:36386-36396.
29. Shao C, Roberts K N, Markesbery W R, Scheff S W, Lovell M A (2006) Oxidative stress in head trauma in aging. Free Radic Biol Med 41:77-85.
30. Shi R, Luo J, Peasley M A (2002) Acrolein inflicts axonal membrane disruption and conduction loss in isolated guinea pig spinal cord. Neuroscience 115:337-340.
31. Shibata N, Nagai R, Miyata S, Jono T, Horiuchi S, Hirano A, Kato S, Sasaki S, Asayama K, Kobayashi M (2000) Nonoxidative protein glycation is implicated in familial amyotrophic lateral sclerosis with superoxide dismutase-1 mutation. Acta Neuropathol (Berl) 100:275-284.
32. Shields D C, Banik N L (1999) Pathophysiological role of calpain in experimental demyelination. J Neurosci Res 55:533-541.
33. Shields D C, Schaecher K E, Saido T C, Banik N L (1999) A putative mechanism of demyelination in multiple sclerosis by a proteolytic enzyme, calpain. Proc Natl Acad Sci USA 96:11486-11491.
34. Smith K J, Kapoor R, Felts P A (1999) Demyelination: the role of reactive oxygen and nitrogen species. Brain Pathol 9:69-92.
35. Trapp B D, Nave K A (2008) Multiple sclerosis: an immune or neurodegenerative disorder? Annu Rev Neurosci 31:247-269.
36. Trapp B D, Ransohoff R, Rudick R (1999) Axonal pathology in multiple sclerosis: relationship to neurologic disability. Curr Opin Neurol 12:295-302.
37. Trapp B D, Peterson J, Ransohoff R M, Rudick R, Mork S, Bo L (1998) Axonal transection in the lesions of multiple sclerosis. N Engl J Med 338:278-285.
38. Uchida K, Kanematsu M, Morimitsu Y, Osawa T, Noguchi N, Niki E (1998a) Acrolein is a product of lipid peroxidation reaction. Formation of free acrolein and its conjugate with lysine residues in oxidized low density lipoproteins. J Biol Chem 273:16058-16066.
39. Uchida K, Kanematsu M, Sakai K, Matsuda T, Hattori N, Mizuno Y, Suzuki D, Miyata T, Noguchi N, Niki E, Osawa T (1998b) Protein-bound acrolein: potential markers for oxidative stress. Proceedings of the National Academy of Sciences of the United States of America 95:4882-4887.
40. Wood P L, Khan M A, Moskal J R, Todd K G, Tanay V A, Baker G (2006) Aldehyde load in ischemia-reperfusion brain injury: neuroprotection by neutralization of reactive aldehydes with phenelzine. Brain Res 1122:184-190.
41. Bautista D. M., Jordt S. E., Nikai T., Tsuruda P. R., Read A. J., Poblete J., Yamoah E. N., Basbaum A. I., and Julius D. (2006) TRPA1 mediates the inflammatory actions of environmental irritants and proalgesic agents. Cell. 124, 1269-1282.
42. Burcham P. C., Kerr P. G., and Fontaine F. (2000) The antihypertensive hydralazine is an efficient scavenger of acrolein. Redox Rep. 5, 47-49.
43. Hamann K., Nehrt G., Ouyang H., Duerstock B., and Shi R. (2008) Hydralazine inhibits compression and acrolein-mediated injuries in ex vivo spinal cord. J Neurochem. 104, 708-718.
44. Leung G., Sun W., Zheng L., Brookes S., Tully M., and Shi R. (In press) Anti-acrolein treatment improves behavioral outcome and alleviates myelin damage in EAE mouse. Neuroscience.
45. Liu-Snyder P., Borgens R. B., and Shi R. (2006) Hydralazine rescues PC12 cells from acrolein-mediated death. J Neurosci Res. 84, 219-227.
46. Luo J., Uchida K., and Shi R. (2005) Accumulation of acrolein-protein adducts after traumatic spinal cord injury. Neurochem Res. 30, 291-295.

What is claimed is:

1. A unit dosage form for treating pain, the unit dosage form comprising one or more fused hydrazinopyridazines in a therapeutically effective amount for treating a patient with a pain disorder, wherein the one or more fused hydrazinopyridazines are the only active ingredients in a therapeutically effective amount for treatment of pain in the unit dosage, and wherein the at least one fused hydrazinopyridazine is a compound of the formula

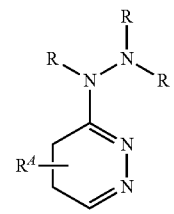

or a pharmaceutically acceptable salt thereof, wherein:

R is independently selected in each instance from hydrogen, acyl, or sulfonyl; or alkyl, alkenyl, alkynyl, cycloalkyl, cycloalkenyl, heteroalkyl, heteroalkenyl, cycloheteroalkyl, cycloheteroalkenyl, aryl comprising 3-10 ring members, heteroaryl comprising 3-10 ring members, arylalkyl comprising 3-10 ring members, or heteroarylalkyl comprising 3-10 ring members, each of which is optionally substituted; and $R^4$ represents three substituents, one of which is selected from the group consisting of hydrogen, halo, hydroxy and derivatives thereof, amino and derivatives thereof, thio and derivatives thereof, acyl, carboxylate or a derivative thereof, hydroxylamino and derivatives thereof, hydrazino and derivatives thereof, sulfinyl or a derivative thereof, or sulfonyl or a derivative thereof; or alkyl, alkenyl, alkynyl, cycloalkyl, cycloalkenyl, heteroalkyl, heteroalkenyl, cycloheteroalkyl, cycloheteroalkenyl, aryl comprising 3-10 ring members, heteroaryl comprising 3-10 ring members, arylalkyl comprising 3-10 ring members, or heteroarylalkyl comprising 3-10 ring members, each of which is optionally substituted; and two of $R^A$ are taken together with the attached carbons to form an optionally substituted saturated, unsaturated, or aromatic carbocycle or heterocycle.

2. The unit dosage form of claim 1 wherein the unit dosage comprises a compound that is selected from the group consisting of hydralazine, dihydralazine, endralazine, todralazine, and budralazine, and combinations thereof.

3. The unit dosage form of claim 1 wherein $R^A$ represents a hydrogen; or $R^A$ includes an optionally substituted benzo group; or $R^A$ includes an optionally substituted fused piperidine; or $R^A$ includes a hydrazino or derivative thereof; or $R^A$ includes a hydrazino; or $R^A$ includes amino or a derivative thereof; or $R^A$ includes dialkylamino, where each alkyl is independently selected, and independently optionally substituted.

4. The unit dosage form of claim 3 wherein each R is hydrogen; or at least one R is acyl; or at least one R is optionally substituted alkoxycarbonyl.

5. The unit dosage form of claim 4 wherein each R is hydrogen.

6. The unit dosage form of claim 4 wherein at least one R is acyl.

7. The unit dosage form of claim 4 wherein at least one R is optionally substituted alkoxycarbonyl.

8. The unit dosage form of claim 1 wherein the fused hydrazinopyridazine, is included at a dose that is not therapeutically effective or clinically effective for treating hypertension, in a single or divided format.

9. The unit dosage form of claim 1 wherein the fused hydrazinopyridazine is included at a dose that is not therapeutically effective or clinically effective for treating depression, in a single or divided format.

10. The unit dosage form of claim 1 wherein the fused hydrazinopyridazine is included at a dose that is not therapeutically effective or clinically effective for treating anxiety, in a single or divided format.

11. A composition comprising a fused hydrazinopyridazine in a therapeutically effective amount for treating a patient with a pain disorder, wherein the one or more fused hydrazinopyridazines are the only active ingredients in a therapeutically effective amount for treatment of pain in the composition, and wherein the fused hydrazinopyridazine is a compound of the formula

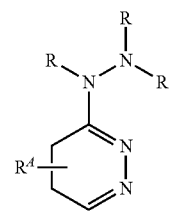

or a pharmaceutically acceptable salt thereof, wherein:

R is independently selected in each instance from hydrogen, acyl, or sulfonyl; or alkyl, alkenyl, alkynyl, cycloalkyl, cycloalkenyl, heteroalkyl, heteroalkenyl, cycloheteroalkyl, cycloheteroalkenyl, aryl comprising 3-10 ring members, heteroaryl comprising 3-10 ring members, arylalkyl comprising 3-10 ring members, or heteroarylalkyl comprising 3-10 ring members, each of which is optionally substituted; and $R^A$ represents three substituents, one of which is selected from the group consisting of hydrogen, halo, hydroxy and derivatives thereof, amino and derivatives thereof, thio and derivatives thereof, acyl, carboxylate or a derivative thereof, hydroxylamino and derivatives thereof, hydrazino and derivatives thereof, sulfonyl or a derivative thereof, or sulfonyl or a derivative thereof; or alkyl, alkenyl, alkynyl, cycloalkyl, cycloalkenyl, heteroalkyl, heteroalkenyl, cycloheteroalkyl, cycloheteroalkenyl, aryl comprising 3-10 ring members, heteroaryl comprising 3-10 ring members, arylalkyl comprising 3-10 ring members, or heteroarylalkyl comprising 3-10 ring members, each of which is optionally substituted; and two of $R^A$ are taken together with the attached carbons to form an optionally substituted saturated, unsaturated, or aromatic carbocycle or heterocycle.

12. The composition of claim 11 wherein $R^A$ represents a hydrogen; or $R^A$ includes an optionally substituted benzo group; or $R^A$ includes an optionally substituted fused piperidine; or $R^A$ includes a hydrazino or derivative thereof; or $R^A$ includes a hydrazino; or $R^A$ includes amino or a derivative thereof; or $R^A$ includes dialkylamino, where each alkyl is independently selected, and independently optionally substituted.

13. The composition of claim 12 wherein each R is hydrogen; or at least one R is acyl; or at least one R is optionally substituted alkoxycarbonyl.

14. The composition of claim 13 wherein each R is hydrogen.

15. The composition of claim 13 wherein at least one R is acyl.

16. The composition of claim 13 wherein at least one R is optionally substituted alkoxycarbonyl.

17. The composition of claim 11 wherein the fused hydrazinopyridazine, is selected from the group consisting of hydralazine, dihydralazine, and endralazine.

* * * * *